United States Patent
Biddick et al.

[11] Patent Number: 5,855,307
[45] Date of Patent: Jan. 5, 1999

[54] INHALER HOLSTER

[76] Inventors: Joan F. Biddick; Sean T. Biddick, both of 37 Columbia La., Jamestown, R.I. 02835

[21] Appl. No.: 984,068

[22] Filed: Dec. 3, 1997

[51] Int. Cl.⁶ .......................................... A45F 5/00
[52] U.S. Cl. ........................ 224/267; 224/148.6; 224/219; 224/242; 224/250; 128/205.22
[58] Field of Search ................................. 224/148.1, 148.5, 224/148.4, 148.6, 219, 220, 221, 222, 267, 191, 242, 245, 250; 222/175; D3/229; 362/103; 128/205.22

[56] References Cited

U.S. PATENT DOCUMENTS

| D. 272,581 | 2/1984 | Petroff | D3/71 |
|---|---|---|---|
| D. 293,857 | 1/1988 | Stout et al. | D3/106 |
| D. 306,800 | 3/1990 | Yeager | D3/100 |
| D. 328,820 | 8/1992 | Davie | D3/229 |
| D. 345,861 | 4/1994 | Knox et al. | D3/203 |
| D. 375,624 | 11/1996 | Jensen | D3/229 |
| D. 377,861 | 2/1997 | Jacober | D3/203 |
| 4,966,322 | 10/1990 | Zagorski et al. | 224/267 |
| 4,974,762 | 12/1990 | Boretsky et al. | 224/222 |
| 5,060,835 | 10/1991 | Payne | 224/250 |
| 5,395,023 | 3/1995 | Naymark et al. | 224/245 |
| 5,730,118 | 3/1998 | Hermanson | 128/205.22 |

FOREIGN PATENT DOCUMENTS

| 92022463 A | 12/1992 | WIPO | 224/219 |
|---|---|---|---|

*Primary Examiner*—Gary E. Elkins
*Assistant Examiner*—Gregory M. Vidovich
*Attorney, Agent, or Firm*—Patent & Trademark Service; Thomas Zack; Joseph H. McGlynn

[57] ABSTRACT

An inhaler or container holster which is strapped around a user's wrist and ready to use, End hook and loop fasteners on a wrist band hold an inhaler band to the user's wrist band while a second set of hook and loop end fasteners on an inhaler band hold the inhaler, The wrist band is generally perpendicular to the inhaler band which either totally or partially encircles and holds the canister containing the inhaler. The canister's end segments may be additionally secured to the inhaler band by elastic strap assemblies attached to the inhaler band which loop around the top and bottom of the canister at opposite ends. Ventolin or any other asthma or any other medication may be placed in the inhaler or container.

6 Claims, 1 Drawing Sheet

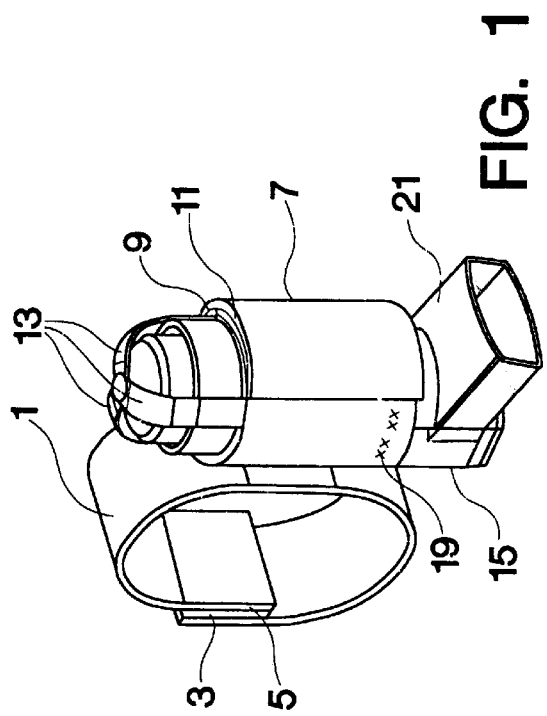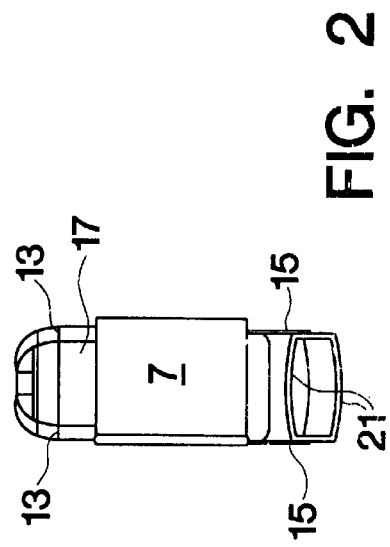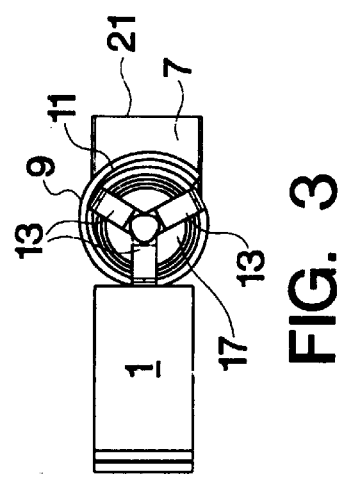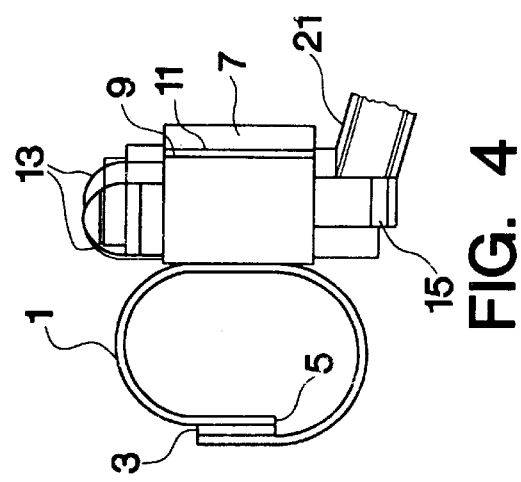

INHALER HOLSTER

BACKGROUND OF THE INVENTION

Persons with respiratory difficulties, such as asthma, often need the use of an inhaler to provide relief from breathing problems. This inhaler with its solution (e.g., Ventolin ) should be readily accessible to the user and is usually carried in one's pocket or purse to insure the same easy accessibility. However, when a person is exercising there may be no pockets in their shorts for the inhaler necessitating its being carried in their sock or hand while attempting to exercise or left with a friend or coach. While these attempts to provide ready inhaler accessibility to exercising asthma suffers have some merit, the present invention provides a better more accessible solution by providing for a wrist held inhaler that can be carried by the user and used without taking the inhaler out of its wrist mount all as more fully described hereafter.

DESCRIPTION OF THE PRIOR ART

Holders for medical supplies are well known. For example, in U.S. Pat. Des. 272,581 a closable box-like medical supply pack with a carrying strap is depicted.

The Stout et al. reference, U.S. Pat. Des. 293,857 shows a holster for a pharmaceutical bottle having a belt engaging loop and an openable pocket for mounting the bottle.

In the Yeager invention (U.S. Pat. Des 306,800) an insulin protector is illustrated having an outer flapped pocket with a zipper openable top.

The Knox et al. reference (U.S. Pat. Des. 345,861) shows a nurse purse having a belt that supports a purse with the purse having opened outer vital holding horizontal pockets on the purse's surface.

And in U.S. Pat. Des. 377,861 to Jacober a top zippered inhaler carrying case is depicted having a belt attachment on its back side. In contrast to these holders the present invention provides for a wrist inhaler holder that can conveniently be carried by a user while exercising and used by them without having to dismount the inhaler from its holder all as more further set forth in this specification.

SUMMARY OF THE INVENTION

This invention relates to an inhaler holster which is strapped around a user's wrist. End hook and loop fasteners on a wrist band hold the holster to the wrist while a second hook and loop fastener generally perpendicular to the wrist band on a second band act to enclose the canister containing the inhaler. The canister's ends may be additionally secured to the first wrist band by elastic straps attached to the band which wrap around the canister on opposite ends, It is the primary object of the present invention to provide for an improved inhaler holding apparatus that is secured to the wrist of a user.

Another object is to provide for such a holder wherein a first set of hook and loop end fasteners retain the wrist's band to a user and a second set of hook and loop fasteners retain the inhaler canister to the wrist band.

These and other objects and advantages of the present invention will become apparent to readers from a consideration of the ensuing description and the accompanying drawings.

BRIEF DESCRIPTION OF THE DRAWINGS

FIG. 1 is a perspective side view of the invention's preferred embodiment.

FIG. 2 is a front view of the FIG. 1 embodiment.

FIG. 3 is a top view of the FIG. 1 embodiment.

FIG. 4 is a side view of the FIG. I embodiment.

DESCRIPTION OF THE PREFERRED EMBODIMENT

FIG. 1 is a perspective side view of the invention's preferred embodiment. An elongated flexible wrist band 1 has engaged hook and loop end pad fasteners designated by the numbers 3 and 5 forming a closed loop configuration. The hook or loop material forming the pad 5 is located on the opposite side surface from the pad material 3 to permit the engagements of the two pads when the band is wrapped around a user's wrist. Of course the positions of the two pads could be reversed as long as one is on the opposite band side surface from the other. In this way the hook and loop surfaces on each pad can engage each other to fastener the band. Hook and pile material is included in the term hook and loop material used for these end fastener's as well as the trade name term VELCRO™ material or VELCRO™ end fasteners.

Appropriately perpendicularly oriented to the first wrist band material is a second inhaler band 7 which also has hook and loop end fasteners to permit the inhaler band to loop around and partially encircle the inhaler and fasten around it.

The second inhaler band 7 is fixed to the first wrist band 1 near its center by stitching or some other permanent fastening means such as a bonding material, rivets, etc. As best shown in FIG. 1 the second inhaler band is fastened at its engaged ends to form a closed loop in which an inhaler container can be held. One of the two engaging band end pads (9) forming the fasteners for the inhaler's band is partially shown in FIG. 1. The other end pad 11 engaging pad 9 is also partially visible and under the surface of band 7 on the opposite side from pad 9 near the end of the band.

Located on opposite sides of the band 7 are two elastic loop straps assemblies 13 and 15. Each of these two straps assemblies form one or more loops and are fastened to the band 7 under the inhaler using conventional fastening means such as stitching, bonding material, rivets, etc. These two elastic strap assemblies serve as additional inhaler canister/container holding members which engage the canister 17 near its upper and lower end segments. The fastener stitching 19 in the inhaler band 7 used to hold this band to the lower strap assembly 15 can be seen.

FIG. 2 is a front view of the FIG. 1 embodiment facing the inhaler canister 17 with Ventolin or another medication contained within it and shown mounted vertically on the band 7. The previously mentioned upper and lower loop straps assemblies 13 and 15, respectively, are also depicted. Two of the three elastic straps for upper assembly 13 are shown as well as the single elastic loop for lower strap assembly 15. The two engaged inhaler hook and loop (or hook and pile) facing pads 9 and 11 are behind the band 7 and therefore not visible in this view.

FIG. 3 is a top view of the FIG. 1 embodiment. In this view the three loops for upper strap assembly 13 are clearly visible along with the mounted inhaler's lower opened extension 21.

FIG. 4 is a side view of the FIG. 1 embodiment. The closed loop configuration of the adjustable wrist band 1 is displayed as well as the band 7 attached upper and lower straps assemblies 13 and 15.

In use, a user would fasten the canister 17 to the wrist band 1 by looping the inhaler band 7 over the canister as the two elastic end straps assemblies 13 and 15 are expanded to fit over and under around the canister as described and hold it when in a relaxed constricted position. After engaging the wrist band's hook and loop fasteners to form a loop around the canister, the user would then place the opened holder band 1 around their wrist. To do so, the user would wrap the wrist band around his or her wrist and fasten the band to close it on the wrist with the two end fastener pads 3 and 5.

When needed, such as in an asthma attack, the user could simply raise his or her arm with canister on it to a position adjacent one's mouth or nose and with the other free hand press or squeeze the held canister to eject the necessary relief from it in the form of a spray or mist as is appropriate for the particular medication to be delivered. There is no hunting or looking for the proper medication or waiting for It to be delivered since the medication is being carried by the user on their person. Thus, there is no delay in the delivery of needed relief.

While not in use, the transported medication permits the hands of the user to be free and fully participate in any exercise or sport since the inhaler holder is no more obtrusive than a wrist watch and just as easy to carry. Clearly, other medications could also be carried in the inhaler including those that are to be taken orally in a liquid form as well as those to be sprayed in a mist form. Cosmetics or other sprayable material could also be placed in the inhaler for use. The low cost of producing this inhaler holder combined with its great versatility and marked need for those that exercise and may need the prompt delivery of medications should be readily apparent to all.

Although the present invention's preferred embodiment and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A container holder in combination with a container containing medication, the container holder comprising:
    an elongated wrist band having opposing ends and a longitudinal axis extending therebetween, each of said ends having fastening means for securing said wrist band around a wrist of a user;
    an elongated inhaler band having opposing ends, opposing longitudinal edges and a longitudinal axis extending therebetween, said inhaler band attached to said wrist band such that said axis of said inhaler band is at approximately a right angle to said axis of said wrist band, said ends of said inhaler band having fastening means for securing said inhaler band around a mid portion of the container; and
    at least one elastic strap member extending substantially perpendicular from each longitudinal edge of the inhaler band, said strap members adapted to respectively loop around opposite ends of the container to further secure the container to the holder.

2. A container holder as defined in claim 1, wherein the fastening means of said wrist band comprise hook and loop pads attached to opposite side surfaces of said wrist band.

3. A container holder as defined in claim 1, wherein the fastening means of said inhaler band comprise hook and loop pads attached to opposite side surfaces of said inhaler band.

4. A container holder as defined in claim 1 wherein said inhaler band is attached to said wrist band by means of stitching.

5. A container holder as defined in claim 1 wherein said container is an inhaler.

6. A container holder as defined in claim 5 wherein the medication is for the treatment of asthma which is deliverable in a spray to a user.

* * * * *